United States Patent
Chueng et al.

(10) Patent No.: US 9,866,742 B2
(45) Date of Patent: Jan. 9, 2018

(54) CAMERA SYSTEM FOR SURGICAL APPLICATIONS

(71) Applicant: Smith & Nephew, Inc., Memphis, TN (US)

(72) Inventors: Lim Chueng, Concord, MA (US); Garry Womack, Edmond, OK (US); Jonathan Yuen, Arlington, MA (US)

(73) Assignee: Smith & Nephew, Inc., Memphis, TN (US)

( * ) Notice: Subject to any disclaimer, the term of this patent is extended or adjusted under 35 U.S.C. 154(b) by 116 days.

(21) Appl. No.: 14/732,852

(22) Filed: Jun. 8, 2015

(65) Prior Publication Data

US 2015/0271384 A1 Sep. 24, 2015

Related U.S. Application Data

(63) Continuation of application No. 12/598,643, filed as application No. PCT/US2008/062628 on May 5, 2008, now Pat. No. 9,107,598.

(60) Provisional application No. 60/915,997, filed on May 4, 2007.

(51) Int. Cl.
- *H04N 5/232* (2006.01)
- *H04N 5/225* (2006.01)
- *A61B 1/00* (2006.01)
- *A61B 1/04* (2006.01)
- *H04N 5/217* (2011.01)

(52) U.S. Cl.
CPC ..... *H04N 5/23203* (2013.01); *A61B 1/00059* (2013.01); *A61B 1/042* (2013.01); *H04N 5/2178* (2013.01); *H04N 5/2252* (2013.01); *H04N 5/23229* (2013.01); *H04N 2005/2255* (2013.01)

(58) Field of Classification Search
CPC .. A61B 1/00059; A61B 1/042; H04N 5/2178; H04N 5/2252; H04N 5/23203; H04N 5/23229; H04N 2005/2255
See application file for complete search history.

(56) References Cited

U.S. PATENT DOCUMENTS

| | | | | |
|---|---|---|---|---|
| 5,528,261 A * | 6/1996 | Holt | ........................ | G09G 5/02 345/604 |
| 6,542,185 B1 * | 4/2003 | Bogardus | ............... | H04N 9/735 348/188 |
| 6,724,422 B1 * | 4/2004 | Werner | ................... | H04N 1/603 348/187 |
| 8,234,578 B2 * | 7/2012 | Ferren | ...................... | G06F 3/017 345/156 |
| 2006/0139881 A1 * | 6/2006 | Jan | ........................ | F04D 29/541 361/697 |
| 2007/0076957 A1 * | 4/2007 | Wang | ................. | G06K 9/00234 382/195 |
| 2008/0002023 A1 * | 1/2008 | Cutler | .................... | G06T 3/4038 348/36 |
| 2008/0086033 A1 * | 4/2008 | Mihalca | ............. | A61B 1/00105 600/160 |
| 2008/0139881 A1 * | 6/2008 | Cover | ................ | A61B 1/00016 600/103 |

* cited by examiner

*Primary Examiner* — Abdullahi E Salad (57) ABSTRACT

The present disclosure relates to a camera system for use in surgical applications. The camera system comprises an image processor; and an imaging device coupled to the image processor, wherein calibration of the imaging device occurs automatically upon coupling the imaging device to the image processor. A method of transmitting data is also disclosed.

17 Claims, 4 Drawing Sheets

| CORRECTION | ESTIMATED MEMORY SPACE FOR PARAMETERS |
|---|---|
| BLEMISH | 32 LOCATIONS X 3 CHANNELS X 21 BIT |
| BLACK PEDESTAL | 960 LOCATIONS X 3 CHANNELS X 8 BIT |
| | 540 LOCATIONS X 3 CHANNELS X 8 BIT |
| WHITE SHADING | 960 LOCATIONS X 3 CHANNELS X 12 BIT |
| | 540 LOCATIONS X 3 CHANNELS X 12 BIT |
| WHITE BALANCE | 2 X 12 BIT LAST VALID R AND B GAIN VALUES |
| COLOR MATCHING | 3 X 3 X 12 BITS |
| ELC | 1 X 12 BIT SENSITIVITY NORMALIZATION FACTOR |
| RGB SPATIAL INTERPOLATION | NONE |
| RGB TO YCbCr | NONE |
| HORIZONTAL APERTURE CORRECTION | NONE |
| MOTION ADAPTIVE DEINTERIACING | 2 X 16 BIT MOTION DETECTION THRESHOLDS |
| VERTICAL APERTURE CORRECTION | NONE |
| UNSHARP MASKING | NONE |
| CORING | 12 BIT THRESHOLD |
| LEVEL DEPENDENDENT NOISE SUPPRESSION | 12 BIT THRESHOLD |
| DIGITAL ZOOM | NONE |
| YCrCb to RGB | NONE |
| RGB TO HSV | NONE |
| HUE CONTROL | 360 ELEMENT X 8 BIT DEFAULT HUE DELTA VALUES |
| SATURATION CONTROL | 360 ELEMENT X 12 BIT DEFAULT SATURATION GAIN VALUES |
| HSV TO RGB | NONE |
| GAMMA/KNEE/DECIMATION | NONE |
| HOUR METER | 4 BYTES |
| CAMERA SERIAL NUMBER | 4 BYTES |
| SPARE | 1024 BYTES (TBD) |

FIG.3

| PARAMETERS | ESTIMATED MEMORY SPACE |
|---|---|
| BLEMISH | 32 LOCATIONS X 3 CHANNELS X 21 BIT |
| BLACK PEDESTAL | 960 LOCATIONS X 3 CHANNELS X 8 BIT<br>540 LOCATIONS X 3 CHANNELS X 8 BIT |
| WHITE SHADING | 960 LOCATIONS X 3 CHANNELS X 16 BIT<br>540 LOCATIONS X 3 CHANNELS X 16 BIT |
| WHITE BALANCE | 3 X 16 BITS |
| COLOR MATCHING | 3 X 3 X 16 BITS ( FROM HEAD )<br>3 X 3 X 16 BITS ( FOR COMBINE WITH WHITE BALANCE ) |
| ELC | 4 POSSIBLE USER ROIs X 2 (szx,szy) X 16 BIT<br>2 X 16 BIT RANGE THRESHOLD<br>3 X 16 BIT BIN THRESHOLD<br>1 X 16 INTEGRATION DELTA<br>1 X 16 BIT INTEGRATION DELTA GAIN FACTOR<br>1 X 16 BIT SENSITIVITY NORMALZATION FACTOR |
| RGB SPATIAL INTERPOLATION | NONE |
| RGB TO YCbCr | 3 x 3 x 16 BIT |
| HORIZONTAL APERTURE CORRECTION | 31 X 16 BIT X M X N USER SETTINGS<br>WHERE M= BAND N = BOOST FACTOR |
| MOTION ADAPTIVE DEINTERLACING | 11 COL X 3 ROW X 16 BIT LPF COEFFICIENTS<br>2 X 16 BIT MOTION DETECTION THRESHOLDS (FROM HEAD)<br>2 X 16 BIT SCALING VALUES FOR TEMPORAL FILTER SECTION |
| VERTICAL APERTURE CORRECTION | 5 X 16 BIT X M X N USER SETTINGS<br>WHERE M = BAND N = BOOST FACTOR |
| UNSHARP MASKING | 16 BIT SCALE FACTOR<br>31 COLS X 5 ROWS X 16 BIT COEFFICIENTS |
| CORING | 31 X 16 BIT COEFFICIENTS<br>16 BIT THRESHOLD |
| LEVEL DEPENDENT NOISE SUPPRESSION | 16 BIT THRESHOLD |
| DIGITAL ZOOM | 16 BIT FIELD DETECTION THRESHOLD |
| YCrCb to RGB | 3 X 3 X 16 BIT CONVERSION MATRIX |
| RGB TO HSV | NONE |
| HUE CONTROL | 360 ELEMENT X 8 BIT DEFAULT HUE DELTA VALUES<br>8 USER SETTINGS X 6 PHASE X 8 BIT HUE DELTA VALUES<br>1 REAL TIME X 6 X 8 BIT HUE DELTA VALUES |
| SATURATION CONTROL | 360 ELEMENT X 12 BIT DEFAULT SATURATION GAIN VALUES<br>10 USER SETTINGS X 6 PHASE X 16 BIT HUE DELTA VALUES<br>1 REAL TIME X 6 X 16 BIT HUE DELTA VALUES |
| HSV TO RGB | NONE |
| GAMMA/KNEE/DECIMATION | 4 TABLES X $2^{12}$ DEPTH X 10 BIT<br>GAMMA OFF<br>GAMMA/KNEE LOW<br>GAMMA/KNEE NORMAL<br>GAMMA/KNEE HIGH |
| HOUR METER | 4 BYTES |
| CAMERA SERIAL NUMBER | 4 BYTES |

FIG. 4

| CORRECTION | ESTIMATED MEMORY SPACE |
|---|---|
| BLEMISH | NONE |
| BLACK PEDESTAL | NONE |
| WHITE SHADING | 960 LOCATIONS X 540 X 3 CHANNELS X 12 BIT |
| WHITE BALANCE | NONE |
| COLOR MATCHING | NONE |
| ELC | NONE |
| RGB SPATIAL INTERPOLATION | NONE |
| RGB TO YCbCr | NONE |
| HORIZONTAL APERTURE CORRECTION | NONE |
| MOTION ADAPTIVE DEINTERLACING WITH TEMPORAL FILTRATION | 2 X 1920 X 540 X 12BIT<br>2 X 1920 X 1080 12 BIT |
| VERTICAL APERTURE CORRECTION | NONE |
| UNSHARP MASKING | NONE |
| CORING | NONE |
| LEVEL DEPENDENT NOISE SUPPRESSION | NONE |
| DIGITAL ZOOM | 2 X 1920 X 1080 X 36 BIT |
| YCrCb to RGB | NONE |
| RGB TO HSV | NONE |
| HUE CONTROL | NONE |
| SATURATION CONTROL | NONE |
| HSV TO RGB | NONE |
| GAMMA/KNEE/DECIMATION | NONE |
| FRAME STORGE* | 1920 X 1080 X 36 BIT |

FIG.5

CAMERA SYSTEM FOR SURGICAL APPLICATIONS

CROSS-REFERENCE TO RELATED APPLICATION

This application is a continuation of U.S. application Ser. No. 12/598,643, filed on Nov. 3, 2009, which is a U.S. National Stage Application, submitted under 35 U.S.C. 371, claiming priority to PCT International Patent Application PCT/US2008062628 filed on May 5, 2008, which claims priority to U.S. Patent Application No. 60/915,997 filed on May 4, 2007, the disclosures of which are incorporated herein by reference in their entireties.

BACKGROUND

1. Technical Field

The present disclosure relates to a camera system for use during surgery and, more particularly, a camera system for use during minimally-invasive surgery.

2. Related Art

Currently, video camera system design for surgical applications has to meet a number of challenging requirements imposed by operating conditions that are not encountered in other professional video applications. These include considerations in areas such as patient safety related to leakage current and electromagnetic interference and compatibility, ease of use by surgeons, a compact size that minimizes clutters around the operating tables, consistent image quality while maintaining interoperability of equipment with different optics and camera control electronics in different operating rooms, elimination of fogging in wet environments, and equipment reliability under harsh sterilization conditions. Other requirements may also need to be considered. These requirements translate into engineering challenges in the design and manufacturing of the mechanical housing, optical components, cable interconnect components, and electronics circuitry.

The most unique attribute of an endoscopy camera designed for minimally invasive surgery, driven by the ease of use requirements, is the two-part design where a compact camera head containing an imaging sensor (e.g., charge coupled device or CCD) is separated from the camera control unit (CCU) containing the video processing electronics. The compact head must fit inside the palm of a surgeon, in as small and as non-intrusive a package as possible. The raw, unprocessed video signal must be transmitted through a thin flexible cable, typically four meters long, to the CCU. Present camera systems mostly operate with analog video signal transmission to the CCU, which introduces unit-to-unit variability of image quality. Temporal drifts in the gain, offset and phase properties of the analog electronics in the camera head and the CCU, cable impedance, transmission delay and losses, all contribute to the variability in the system performance and must be compensated. In a typical hospital, the CCU's are fixed in operating rooms, while the camera head and endoscopes are pooled as they must be sent after each procedure to cleaning and sterilization. The random assignment of camera heads to CCU's presents a challenge to the manufacturers' ability to meet the most important requirement by surgeons, namely, consistently high image quality from procedures to procedures. In many instances, one particular combination of a camera head and a CCU may produce high quality image, while other combinations may be less than satisfactory.

Inconsistent image quality due to mismatch of camera heads and CCU's is one of the most common service problems. This creates a design and manufacturing challenge not encountered in other professional video cameras where the imaging sensors are always packaged, matched to, and calibrated together with the video processing electronics as one single unit. In present endoscopy camera design, which contains many analog electronic components all contributing to a distribution of performance characteristics and stacked-up tolerances, an elaborate video signal alignment procedure must be carried out for both the camera head and the CCU in order to compensate for the unit-to-unit variations. Adding to this complexity, an analog camera head has to be aligned using a calibrated CCU, while a CCU must be aligned using a calibrated camera head. The calibrated camera head and the calibrated CCU are carefully selected to be the ideal or "golden" reference, as this term is known to those of skill in the art, camera head or CCU.

Even if this circular and inter-dependent video alignment procedure is successful, residual variability, drifts, and instability over an extended period of time will inevitably lead to mis-alignment between the camera head and CCU. Finally, camera head video alignment and calibration with the camera control unit is performed manually on the manufacturing floor, thereby wasting valuable time. A system is needed such that automatic calibration and alignment can occur once the camera is connected to the camera control unit.

With the introduction of HDTV cameras for endoscopy applications, the above-described problems are compounded by improved image quality requirements, namely, higher resolution, better color accuracy, lower noise, and as much as six times increase in video bandwidth. The higher bandwidth requirements make the transmission of analog video and timing signals, over a four meter cable, much more challenging. Minor variations in cable lengths that can be compensated with analog phase-lock loops in standard definition television become several times more challenging to correct. As bandwidth is increased, noise and other circuit stability problems are compounded. The electrical power dissipation also scales proportionally higher with increased signal bandwidth, thereby leading to increased heat dissipation. In a compact camera head, the heat generated will further increase the operating temperature of the electronics circuit, resulting in yet higher thermally induced noise and drifts.

To overcome the above problems, and in order to ensure the highest image quality commensurate with the expected benefits of HDTV camera, it is desirable to digitize the video signal inside the camera head, so only digital signals, rather than analog signals, need to be transmitted over a cable to the remote CCU. This approach also has the benefit that the video image quality will not be degraded due to noise pickup along the cable, and the CCU electronics will have no analog circuit that is prone to drifts and instability. If the video signal is 100% digital, no manufacturing calibration or video alignment is needed for the CCU during the manufacturing process, thereby saving time and cost. Several technical hurdles must be overcome in order to send digital data to the CCU.

First, the heat generated by the additional analog-to-digital conversion circuitry within a small confined volume must be dissipated. Second, a high quality, high resolution digital HDTV imaging sensor requires as much as fifty bits of bi-directional data transmission between the camera head and CCU. If these fifty bits of data are sent by a traditional cable where one line is dedicated to one bit, the cable diameter will become too large and inflexible for good user ergonomics. The wire count and cable diameter must not be bigger or less flexible than the present camera cable diameter, which is about 6 mm, in order to preserve the ease of use by surgeons. Third, in order to be in compliance with international standards for medical devices on electromagnetic interference and electromagnetic compatibility (EMI/EMC), the emission of electromagnetic radiation due to transmission of high bandwidth digital data along a cable must be contained.

Accommodating video camera electronic components that generate heat energy at a relatively high rate, compared to some standard video cameras, requires that the housing be composed of a material with relatively high thermal conductivity, such as aluminum or an aluminum alloy. If a high thermal conductivity metallic alloy is used for the camera housing, the exterior metallic surface must be electrically isolated. The need to be electrically isolated contradicts the requirement that the interior electronics must be surrounded by an electrically grounded Faraday cage, so as to prevent internally generated electromagnetic interference (EMI) from leaking out of the camera housing and affecting safe operations of other medical electronics used in surgery and patient support. At the same time electromagnetic compatibility (EMC) must be ensured, such that normal camera performance is immune from external electromagnetic interference to a level consistent with international standards for medical devices, such as IEC60601-1-2 for EMI/EMC safety. Furthermore, all the surfaces that may come in contact with the patient must be designed to minimize leakage currents and be insulated to withstand dielectric breakdown to a level required by internationally recognized electrical safety standards, such as the IEC60601 or UL2601 Standards for Electrical Safety. These conflicting requirements therefore require a new approach to the design of the camera housing.

The present video camera systems contain image processors or camera control units that are equipped to process the analog signals from the camera head. As stated above, this analog processing creates unwanted system variables. In addition, as also stated above, alignment and calibration of the camera head currently takes place on the manufacturing floor, rather than automatically upon plug-in of the camera head and the camera control unit. Automatic alignment and calibration of the camera head requires a camera control unit that has the ability to process a number of mathematical algorithms in a particular sequence in real time. Furthermore, as technology evolves, a camera control unit is needed that is easily modifiable to support different types of camera heads.

Therefore, there remains a need for a camera system that can accommodate a camera having a higher definition than standard definition, substantially reduces analog variability in the camera head and camera control unit while preserving image quality, and substantially reduces interactions of head electronics, cable impedance, and camera control unit circuits. In addition, a camera control unit that is easily modifiable to support different types of camera heads and has full control of signal processing algorithms so as to process them in real time is also needed. Furthermore, a system is needed whereby alignment and calibration of the camera head is automatic upon plug-in of the camera to the camera control unit.

SUMMARY

In one aspect, the present disclosure relates to a camera system for use in surgical applications. The camera system comprises an image processor; and an imaging device coupled to the image processor, wherein calibration of the imaging device occurs automatically upon coupling the imaging device to the image processor.

In an embodiment, the camera system further includes an endoscope coupled to the imaging device, the endoscope capable of transmitting an optical image to the imaging device. In another embodiment, the camera system further includes a monitor coupled to the image processor. In yet another embodiment, the imaging device includes a sensor, the sensor receiving the optical image and processing the image into an analog video signal. In a further embodiment, the imaging device further comprises a converter, the converter capable of converting the analog video signal to a digital video signal, the imaging device capable of transmitting the digital video signal to the image processor. In yet a further embodiment, the image processor is capable of receiving the digital video signal and processing the digital video signal.

In an embodiment, the sensor and the image processor both include microprocessors, the sensor microprocessor capable of transmitting data from the imaging device to the microprocessor of the image processor automatically upon coupling the imaging device to the image processor. In another embodiment, the sensor comprises at least one charge-coupled device. In yet another embodiment, the sensor comprises a complimentary-metal oxide-semiconductor imager. In a further embodiment, the imaging device comprises a camera. In yet a further embodiment, the camera comprises a high definition camera. In an embodiment, the image processor comprises a camera control unit. In another embodiment, the imaging device further comprises a means for reducing a size of the imaging device data.

In another aspect, the present disclosure relates to a method of transmitting data comprising providing an imaging device including a sensor, the sensor including a microprocessor; providing an image processor, the image processor including a microprocessor; and coupling the imaging device to the image processor, wherein the sensor microprocessor automatically transmits data from the imaging device to the microprocessor of the image processor.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 4 shows the memory parameters of the CCUµP.

DETAILED DESCRIPTION OF THE EMBODIMENTS

The following description of the preferred embodiment(s) is merely exemplary in nature and is in no way intended to limit the invention, its application, or uses.

Figure 1:
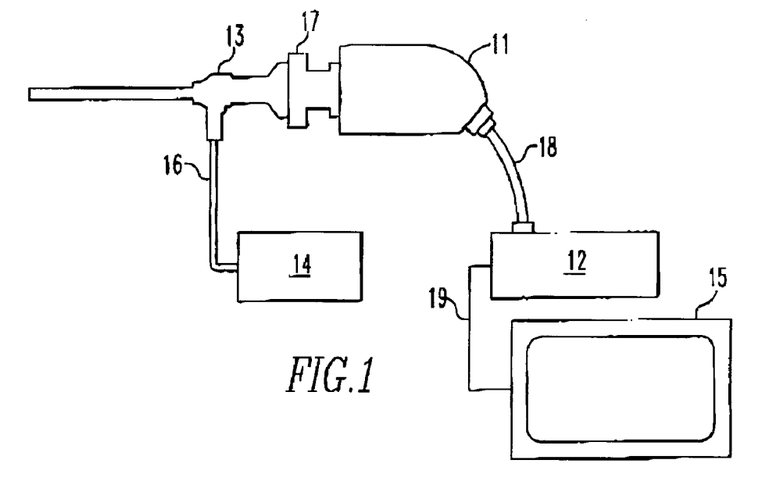
FIG. 1 shows the camera system of the present disclosure as used in a surgical procedure.

The camera system is made up of two subsystems: a remote camera head or imaging device and a digital image processor or camera control unit (CCU). FIG. 1 depicts the imaging device, or camera head 11, and the image processor, or CCU 12, as they may be used in a surgical procedure, such as an endoscopic procedure. The camera head 11, which for the purposes of this disclosure is a high definition camera, produces a digital electronic image from an optical image of a target subject transmitted by way of an endoscope 13, a light source 14, digital image processor 12, and a monitor 15. The light source 14 can be coupled to the endoscope 13 by an optical link 16 to illuminate the target subject under observation beyond the tip of the endoscope 13. In addition, the camera head 11 may be optically coupled to the endoscope 13 by a coupler 17 to receive an optical image, and electrically coupled to an image processor 12 by an electrical link 18 to transmit a resulting digital image, which can then be transmitted by way of another electrical link 19 for display on the monitor 15.

The endoscope 13 that is used with the camera system of the present disclosure is especially suited for high-definition television by featuring diffraction limited MTF and full color correction in the spectral band of between about 436 to about 656 nm. The design of the endoscope 13 utilizes an optical system that includes two rod-lens doublets arranged at both sides of a pupil plane in the first relay system. Each doublet includes two dispersion glasses that allow the endoscope to achieve high level of color correction in the spectral region, as mentioned above. This optical system is further described in U.S. patent application Ser. No. 11/744,810, filed on May 4, 2007, the disclosure of which is incorporated herein by reference in its entirety.

Figure 2:
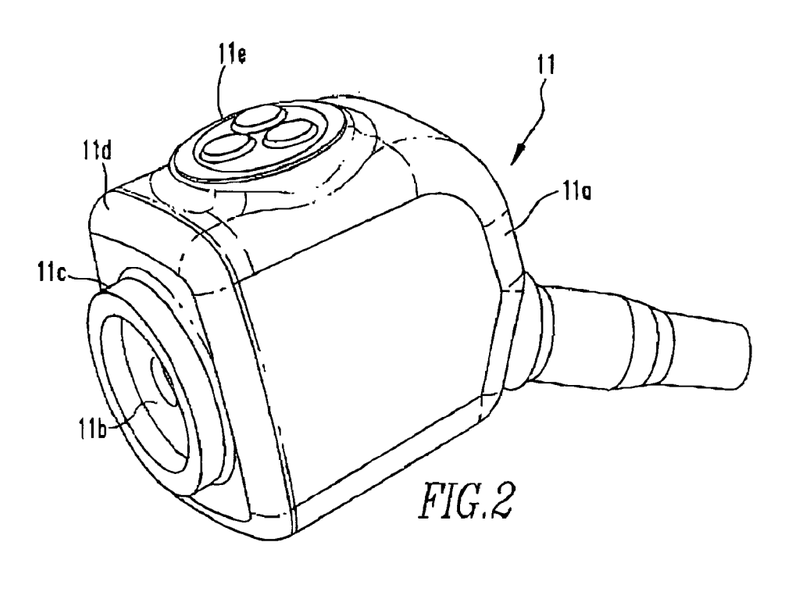
FIG. 2 shows the camera of the present disclosure.

As shown in FIG. 2, the camera head 11 includes a housing 11a enclosing the electrical components of the camera, which may include one or more sensors to transfer an optical image into a digital electronic image, such as three charge-coupled devices (CCDs) configured to image blue, green, and red spectra, and other electronic components as further described below. In order to allow the optical image from a device, such as an endoscope, to pass into the camera head 11, an optical window 11b is attached to housing 11a by way of a bridge 11c at the interface lid between the optical window 11b and the housing 11a.

In order to protect the electronic components of the video camera head 11 during autoclaving, the housing 11a is made from materials having substantial resistance to steam and chemical corrosion. The housing 11a is hermetically sealed to the bridge 11e and the bridge 11c is hermetically sealed to the window 11b via a bonding method such as extrusion welding. The resulting hermetically-sealed video camera head 11 can withstand numerous repeated autoclave cycles, for example, between about one hundred cycles and about one thousand cycles.

Furthermore, in order to accommodate video camera electronic components that generate heat energy at a relatively high rate compared to some standard video cameras, the housing 11a is composed of a material with relatively high thermal conductivity, for example, greater than about 25 Watts per meter kelvin (W/m K), such as aluminum or an aluminum alloy. As a result, the housing 11a dissipates heat at a rate sufficient to maintain an internal ambient at an acceptable working temperature for the electronic components. In addition, aluminum or an aluminum alloy provides a relatively light-weight, low-cost housing 11a with favorable machining properties.

Similarly, the optical window 11b not only has acceptable optical characteristics, but also is able to withstand repeated autoclaving cycles. Thus, the optical window 11b includes an optical ceramic material that is highly transparent and resistant to steam and chemical etching, such as optical sapphire (monocrystalline aluminum oxide, or alumina, $Al_2O_3$). The housing and optical window are more fully described in U.S. patent application Ser. No. 11/539,160, filed Oct. 5, 2006, the disclosure of which is incorporated herein by reference in its entirety.

The head may also be equipped to accommodate optics with a back focal distance of about 20 mm and the size of the head may be about 2 inches in height and width and about 2.5 inches in diameter. There may be buttons 11e located on the camera housing for control of the on-screen manual parameters, such as brightness, zoom, or other surgeon preferences, and peripheral devices, including, without limitation, video recorders.

The camera head 11 of the present disclosure is designed to transmit video data to the CCU in digital format without the need of any analog signal adjustment, thereby eliminating the need for video alignment of the CCU on the manufacturing floor. Any alignment required is performed on the camera head 11. During camera head alignment, all of the resulting calibration factors are stored on a memory (not shown) located in the camera head 11. In addition, a sensor (not shown) is also located in the camera head 11. For the purposes of this disclosure, the sensor is a three charge-coupled device (3-CCD), however, other charge-coupled devices, in addition to other sensors, including, without limitation, a complimentary-metal oxide-semiconductor, are within the scope of this disclosure. The sensor includes a microprocessor. When the head 11 is plugged into the CCU 12, the calibration data is downloaded automatically, via the electrical connection 18, by the sensor microprocessor to a microprocessor (not shown) located in the CCU 12 for subsequent processing. As will be further described later, the calibration data that may be stored in the memory of the camera head 11 is listed in FIG. 3 and the memory requirements of the CCU microprocessor are listed in FIG. 4.

Subsequently, during surgery, the endoscope 13 transmits an optical image to the head 11, specifically to the sensor, and is processed by the sensor resulting in an analog video signal. The analog video signal is converted to a digital video signal by an analog to digital converter (not shown) that is also located in the camera head 11. The converter may be any analog to digital converter known to one of skill in the art. In addition to the converter, the camera head 11 optionally may include a means for reducing a size of the digital video signal (not shown), such as a serializer-deserializer (SERDES), before the digital video signal is transmitted to the CCU 12 by the electrical link 18. As stated above, the digital video signal may contain as many as fifty bits of data, which may cause the diameter of the electrical link 18 to be too large and inflexible. The means susbstantially reduces the size of the digital video signal, therefore substantially reducing the possibility of an increase in the diameter of the electrical link 18.

Once the digital video signal is transmitted to the CCU 12, the signal is processed by a digital video signal processor (not shown) located in the CCU 12. The processed signal is then transmitted via the electrical link 19 to the monitor 15. As will be described below, the memory requirements of the digital video signal processor are listed in FIG. 5.

The only analog circuitry in the CCU 12 is located at the output stage when the digital video signal is converted into several selected analog output formats, such as HD-RGB, Y/C, and Composite, none of which would require adjustment on the manufacturing floor. The CCU is also designed to be able to accommodate, by software re-configuration with minimal hardware changes, sensors from multiple designers and manufacturers.

Figure 3:
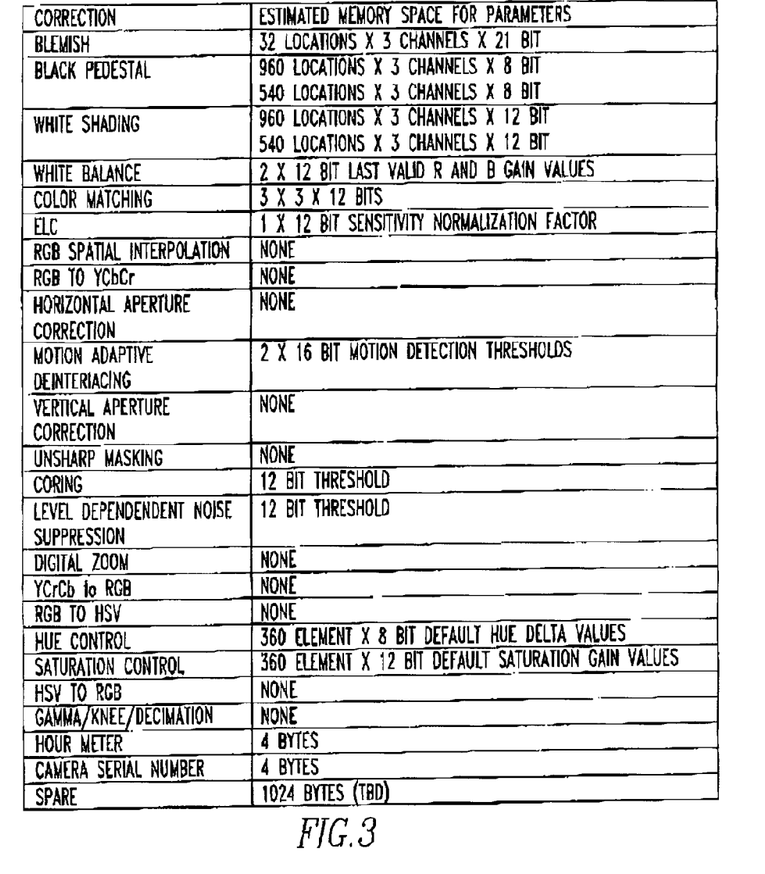
FIG. 3 shows the memory parameters of the camera head.

As stated above, the list of parameters that may be stored in the camera head 11 is given in FIG. 3. Other memory requirements for the CCU microprocessor (CCU μP) are given in FIG. 4 and for the Digital Signal Processor (DSP) are given in FIG. 5. The camera memory requirements are specified in needed bit depth, but it is left up to the head electronics and CCU designers to specify the memory organization.

Figure 5:
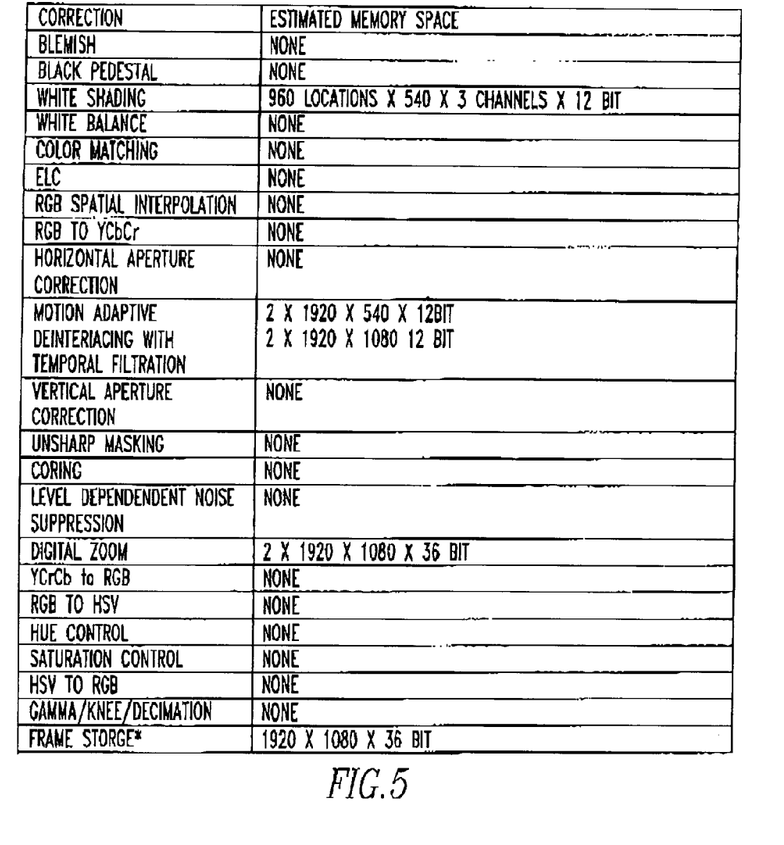
FIG. 5 shows the memory parameters of the DSP.

The features of FIGS. 3, 4, and 5 may be described as the following:

Blemish correction is designed to correct for single pixel defects that contain no recoverable information. Methods of interpolation with a neighborhood metric are substituted into the blemish location. Two methods that may be used are in the cases where single pixel defect locations are permanent or single pixel defect locations vary with time. With regards to permanent defect pixel locations, the blemished correction is performed on known bad pixels with addresses stored on the camera head. Upon plug-in of the camera head to the CCU, the bad pixel addresses are downloaded onto the DSP processor via the CCU μP. The blemish correction algorithm may be the following:

$$S_{R,G,B}(x,y)=[S_{R,G,B}(x-1,y)+S_{R,G,B}(x+1,y)]/2.$$

With regards to time variant defect pixel locations, the blemish correction is performed on the full image frame. No defect pixel location map may be needed. The blemish correction algorithm may be as follows:

$$S_{R,G,B}(x,y)=\text{Median}[S_{R,G,B}(x-1,y),S_{R,G,B}(x,y),S_{R,G,B}(x+1,y)].$$

Black pedestal and black shading correction for direct current (DC) and low frequency spatial variations in the total electronic offset with a sensor respectively. In addition, there is a method for correcting high frequency variations as well. As with DC and low frequency variations, coefficients generated in an offline one time calibration are stored in the camera. The polynomial coefficients are downloaded from the camera head on plug-in to the μP. Six look up tables (LUTs) containing the offset coefficients in the horizontal and vertical directions and in the Red(R), Green(G), and Blue(B) channels, are generated within an external microprocessor (μP) and downloaded into the DSP processor on startup. The generation algorithm may be as follows:

$$LUT1(x_{i,RGB})=\Sigma a_{i,RGB}x_{i,RGB}^n$$

$$LUT2(y_{i,RGB})=\Sigma b_{i,RGB}y_{i,RGB}^n$$

The desired Black Pedestal Value (DC offset) is stored separately in a 1×8 bit word on the camera and downloaded into the DSP processor via the CCU μP for later use. This may be done so that subsequent multiplicative or non-linear gamma operations can be performed with this offset subtracted, and then added back afterward, in order to maintain constant black pedestal (DC) values. In this way, the interaction between black shading and white shading may be substantially reduced.

As with DC, low frequency, and high frequency variations, two one-dimensional LUTs per channel (LUT1 and LUT2) that are generated in an offline one time calibration are stored in the camera. The LUTs are downloaded into the DSP processor from the camera head via the CCU μP on plug-in. Subsequently, the black pedestal and black shading offset values are added pixel-by-pixel to the incoming video by the DSP. The generation algorithm is as follows:

$$S'(x_{i,RGB},y_{i,RGB})=S(x_{i,RGB},y_{i,RGB})+LUT1(x_{i,RGB})+LUT2(y_{i,RGB})+BP\text{desired}$$

With regards to manual fixed white shading, there are two methods for correction. For DC and low frequency variations, coefficients generated in an offline one time calibration are stored in the camera. The polynomial coefficients are downloaded from the camera head on plug-in to the CCU μP. The CCU μP then generates 6 LUT's and loads the DSP. Three full frame gain buffers coefficients are subsequently generated by the DSP in external Synchronous Dynamic Random Access Memory (SDRAM) for use at runtime. The generation algorithm for the frames are the following:

$$G(x,y)=1/(LUT_{1x}+LUT_{2y})$$

Where:

$$LUT1(x_{i,RGB})=\Sigma a_{i,RGB}x_{i,RGB}^n$$

$$LUT2(y_{i,RGB})=\Sigma b_{i,RGB}y_{i,RGB}^n.$$

For the generation of G(x,y), one full frame per channel is generated from the white shading calibration LUTs. The DSP will generate the frames from the 6 loaded LUTs. Each incoming pixel S(x,y) is corrected for white shading while compensating for the desired black pedestal value previously stored. The algorithm is the following:

$$S'(x_{i,RGB},y_{i,RGB})=S(x_{i,RGB},y_{i,RGB})-Bp\text{offset}_{rgb}$$

For manual white balance, the CCU μP must load the default 3×3 color matching coefficients combined with the last valid white balance coefficients (from head) into the DSP before white balance on the DSP can be enabled. The default color matching coefficients are produced by an offline determination of the ideal spectral responses of the video path subsystems (filter, prism, ccd). The default color matching coefficients do not take into account spectral responses of a particular lens subsystem or illuminant. Once the DSP white balance is enabled (DSP must expose an enable bit in the hardware (HW) interface to μP), the DSP performs the white balance determination and exposes the results to the CCU μP via a valid bit. The results are 3 words representing the average response of each channel. The CCU μP then reads the results and normalizes these values to the ideal spectral response coefficients (provided as inputs from an offline calibration tool), the default color matching matrix, and last valid white balance values and loads the combined 3×3 onto the DSP. If the gain coefficients of all the five regions (center, top, bottom, left and right) are close to each other to within about .+−.2% (.+−.2 IRE), then the white shading is within acceptable range. If the gain coefficients are larger, the gain values should then be interpolated in the vertical and horizontal directions to permit automatic white shading to be implemented.

The mathematical description of manual white balance is the following:

$$[R'G'B']=[3\times3\text{Rec709Color Matching Matrix}][\alpha R\gamma G\beta B]$$

The 3×3 Rec.709 Color Matching Matrix is obtained by using a least squares minimization procedure. $\alpha$, $\gamma$, and $\beta$ are the gain coefficients for the respective Red, Green and Blue channels obtained during White Balance operation:

$$\alpha,\gamma,\beta=S_{R,G,B}(v)\tau_{IR}(v)\tau_{Prism}(v)dv/V_{WB}$$

where $S_{R,G,B}$ denotes the CCD spectral sensitivity of the respective Red, Green and Blue CCD channels, $\tau_{IR}$ and $\tau_{Prism}$ represent the spectral transmission of the IR filter and prism block, and $V_{WB}$ represents the measured voltage, integrated over the respective red, green and blue channels during the white balance operations. To preserve the signal amplitude, the components of S and V should be normalized to 1.

Due to the non-telecentricity of the optical system and the desire to use various optical systems with a particular camera head, an additional white shading artifact is introduced which must be compensated for at the time of use in the field. During power up after the white balance is determined during the white balance procedure, the DSP will provide the CCU μPμP sufficient Region of Interests (ROIs) of the data so as to allow the CCU μPμP to perform a separable two dimensional fit in the vertical and horizontal direction relative to the image plane in order to correct for the white shading. The CCU μPμP will generate two LUTs or two sets of coefficients to load into the DSP.

In the DSP, each incoming pixel S(x,y) is corrected for white shading while compensating for the desired black pedestal value previously stored:

$$S'(x_{i,RGB}, y_{i,RGB}) = (S(x_{i,RGB}, y_{i,RGB}) B_{poffset_{rgb}}) \times G(x_{i,RGB}, y_{i,RGB}) + B_{poffset_{rgb}}, \text{ where } G(X_{iRGB}, Y_{iRGB}) = LUT((X_{iRGB}) * LUT(Y_{iRGB}).$$

For the ROI statistics generation, this processing step is not part of the main DSP pipeline but the data is tapped at this point in the pipeline in order to provide statistics from predefined ROIs in the incoming data. The DSP will provide Nx4×16 registers to the CCU μP/DSP interfaces that denote the statistics from each ROI. The DSP will provide RGB and V (in HSV) statistics for each ROI. Furthermore the DSP shall provide Nx1×2 (VALIDROI) registers that correspond to valid, invalidHI, and invalidLOW for each ROI.

For each ROI, the DSP will threshold data within the ROI to determine the validity of the ROI data. Valid data within an ROI will be used in the final statistic for that ROI. For Red, Green, and Blue (ROB) reporting, the DSP will accumulate valid data within an ROI and compute the average signal within each ROI per channel. When V is selected, the DSP will compute V=max(R,G,B), accumulate V and compute the average. Furthermore, the DSP will expose 2×16 bit registers (THRESHOLD_HI and THRESHOLD_LO) to the μP/DSP interface for the purposes of setting the threshold criteria for validity of data within an ROI. It is intended that THRESHOLD_LO be set higher during white balance and auto white shading than during runtime operation. THRESHOLD_HI should be set so as to exclude saturated data within an ROI.

For RGB spatial interpolation, the R and B channels are offset spatially from the G channel by half a pixel horizontally. This applies to 3-CCD prisms supplied by all vendors. In the case where the R and B channels are shifted by half a pixel horizontally, a simple interpolation algorithm is needed, such that the pixel value in between is obtained by averaging the two adjacent physical pixels to the left and right. In the case where the R and B channels are shifted by half a pixel in both the horizontal and vertical directions, the pixel value in between is obtained by averaging the four nearest neighbors.

The algorithm for RGB spatial interpolation is as follows:

$$S'_{rb}(x',y) = S_{rb}(x), (S_{rb}(x) + S_{rb}(x-1))/2, \text{ and } S_{rb}(0);$$

$$S'_{g}(x',y) = S_{g}(x), (S_{g}(x) + S_{g}(x-1))/2, \text{ and } S_{g(end)}$$

As for the conversion of ROB to $YC_RC_B$, color images are typically processed in the RGB color space. For some image enhancement algorithms, there are computational advantages to processing in aluminance-chroma space, such as YCRCB. For example, if the objective is to perform edge-enhancement, it is usually only necessary to apply the enhancement to the luminance component. Due to the high spatial frequency response limitations of human vision, edge enhancement of the chroma components may not be perceptible. At the same time, the chroma elements may be sub-sampled digitally to reduce processing and transmission bandwidth. The luminance component Y is largely dominated by the green intensity. The chroma components, $C_B$ and $C_R$, are obtained from the color differences: $C_B = B - Y$ and $C_R = R - Y$. The notation Y, B and R denote that the component has been gamma-corrected. The conversion is based on the ITU Rec. 709 luma standard adopted for HDTV. The luminance and color difference signals (Y, Cr=0.6350*(R−Y), Cb=0.5389*(B−Y)) are:

$$Y' = 0.213R' + 0.715G' 0.072B'$$

$$Cr' = 0.500R' - 0.454G' - 0.046B'$$

$$Cb = -0.115R' - 0.385G' + 0.500B'$$

For the horizontal aperture correction, there is a 31-tap FIR filter in the horizontal direction that boosts a user selectable horizontal frequency band. For the vertical aperture correction, there is a 5-tap FIR filter in the vertical direction that boosts a user selectable vertical frequency band.

For the horizontal aperture correction, there is a 31-tap FIR filter in the horizontal direction that boosts a user selectable horizontal frequency band. For the vertical aperture correction, there is a 5-tap FIR filter in the vertical direction that boosts a user selectable vertical frequency band.

Unsharp masking is a signal processing technique to enhance contrast and details in the shadows while preserving details in the highlights. It represents a form of dynamic range compression. In mathematical form, one method of implementation may be written as:

$$\text{Output Image} = 1/c\{a \times \text{Input Image} - b \times \text{SMOOTH(Input Image)}\}$$

where SMOOTH is a blurring or low pass filtering operator, a and b are adjustable integer numbers, and c is an integral power of two. To ensure that the output image has the same average luma value as the input, (a−b)/c=1, the degree of sharpening is controlled by the coefficients a and b. Higher enhancement is set by making b closer to a. SMOOTH is implemented by using a convolution kernel of dimensions m×n, with each element set=1. For the high resolution camera, m should be greater than 31 and n should be greater than 5. The final size should be based on resource limitations. Another proposed smoothing filter is a discrete Gaussian filter defined by: $H(u) = Ae^{-u2/(2\sigma^2)}$ in the spatial domain defined as $h(x) = \text{sqrt}(2*pi)*A*e^{(-2*pi2*\sigma^2*x^2)}$.

Level dependent digital noise reduction and coring reduces the noise for regions where the Sound-to-Noise Ratio (SNR) is low, i.e., area where the noise is limited by electronics noise and not photon noise. In the darker region, it is important to have lower noise than to have higher resolution. $YC_RC_B$ to RGB conversion is the inverse of the RGB to. $YC_RC_B$ operation, using the inverse of the 3×3 matrix described in the previous section.

RGB to Hue Saturation Value (HSV) color space conversion can be made more intuitively by independently adjusting the HUE and saturation of each color independently. HUE is one of the three dimensions in some color spaces along with saturation and brightness. In order to isolate the HUE, the incoming RGB data is converted into the HSV color space. Once the data is in HSV space, a hue delta LUT is applied to the hue channel and saturation LUT is applied to the saturation channel. For each pixel in RGB where 0<RGB<1, the corresponding symbols for H, S, and V are the following:

$$V = MAX(R,G,B)$$

$$S = [MAX(R,G,B) - MIN(R,G,B))]/MAX(R,G,B)$$

$$H = 60*([G-B]/[MAX(R,G,B) - MIN(R,G,B))]) \text{ for } R = MAX(R,G,B); 60*(2 + (B-R)/[MAX(R,G,B,) - MIN(R,G,B))]) \text{ for } G = MAX(R,G,B); \text{ and } 60*(4 + (R-G)/[MAX(R,G,B) - MIN(R,G,B))]) \text{ for } B = MAX(R,G,B).$$

As for HSV color saturation and hue control, adjustments may be provided for the following reasons:

Correction for head-to-head colorimetry variations, using factory calibration data obtained as part of the manufacturing alignment/calibration processes. The data are stored with each camera head and downloaded into the CCU on camera plug-in;

Ten different surgical procedure specific colorimetry settings are provided. The offset values for the saturation and hue in the RGBCYM axes are stored in a table in the µP in the CCU;

User input using the Open Source Definition (OSD) Menu control. The user may change the hue and saturation in the RGBCYM axes.

The following equations are applied to adjust colors independently:

$$S(x_{i,HSV}, y_{i,H}) = RGB@HSV(S(xi_{,RGB}, y_{i,RGB}))$$

$$S'(x_{i,H}, y_{i,H}) = S(x_iH, y_{i,H}) + LUT[S(x_i, H, y_{i,H})]$$

$$S'(x_{i,s}, y_{i,s}) = S(x_{i,s}, y_{i,s}) * LUT[S(x_{i,H}, y_{i,H})]$$

$$S'(x_{i,RGB}, y_{i,RGB}) = HSV2RGB(S'(x_{i,HSV}, y_{i,HSV}))$$

LUT is the 360 element look up table generated in an offline calibration. Full resolution hue delta and saturation gain LUTs must be stored on the camera head and downloaded to the DSP via the µP. The µP is responsible for storing 8 lower resolution hue and saturation LUTs for storing user preferences on the CCU. One addition lower resolution LUT is maintained in the CCU for temporary user adjustments to hue and saturation respectively. Table 2 provides specific values.

With regards to the HSV to RGB color space conversion, the following equations may be applied:

$$R = v*(1-s*f)60 < H < 120; v*(1-s)120 < H < 180; v*(1-s) 180 < H < 240; v*(1-s*(1-f))240 < H < 300; V 300 < H < 360;$$

$$G = v*(1-s*(1-f));f0 < H < 60;v \text{ for } S == 0||60 < H < 120;v 120 < H < 180;v*(1-s*f)180 < H < 240;v*(1-s) 240 < H < 300;v*(1-s)300 < H < 360;$$

$$B = v*(1-s)0 < H < 60;v*(1-s)60 < H < 120;v*(1-s*(1-f)) 120 < H < 180V \text{ for } S == 0||80 < H < 240;v 240 < H < 300;v*(1-s*f)300 < 360;$$

Where f=H mod 60

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

We claim:

1. A camera system comprising:
   a remote camera head, the remote camera head comprising:
   a steam and chemical corrosion resistant housing composed of a high thermal conductivity material,
   an optical window composed of an optical ceramic material and attached to the steam and chemical corrosion resistant housing by way of a bridge at an interface lid between the optical window and the steam and chemical corrosion resistant housing, the steam and chemical corrosion resistant housing hermetically sealed to the bridge and the bridge hermetically sealed to the optical window;
   a memory storing camera head alignment calibration factors; and
   a microprocessor; and
   a digital image processor including a memory,
   the remote camera head optically coupled to an endoscope by a coupler to receive an optical image, and the microprocessor of the remote camera head electrically coupled to the digital image processor by an electrical link configured to transmit a resulting digital image.

2. The camera system of claim 1 wherein the steam and chemical corrosion resistant housing is composed of aluminum.

3. The camera system of claim 1 wherein the optical window is composed of an optical sapphire.

4. The camera system of claim 1 wherein the camera head alignment calibration factors include:
   a blemish factor;
   a black pedestal factor;
   a white shading factor; and
   a white balance factor.

5. The camera system of claim 4 wherein the camera head alignment calibration factors further include:
   a color matching factor;
   an ELC factor;
   a RGB spatial interpolation factor; and
   a RGB to YCbCr factor.

6. The camera system of claim 5 wherein the camera head alignment calibration factors further include:
   a horizontal aperture factor;
   a motion adaptive deinteriacing factor;
   a vertical aperture correction; and
   a unsharp masking factor.

7. The camera system of claim 6 wherein the camera head alignment calibration factors further include:
   a coring factor;
   a level dependent noise suppression factor;
   a digital zoom factor; and
   a YCbCr to RGB factor.

8. The camera system of claim 7 wherein the camera head alignment calibration factors further include:
   a RGB to HSV factor;
   a hue control factor;
   a saturation control factor; and
   a HSV to RGB factor.

9. The camera system of claim 8 wherein the camera head alignment calibration factors further include:
   a gamma/knee/decimation factor;
   an hour meter factor;
   a camera serial number; and
   a spare factor.

10. The camera system of claim 1 wherein the memory of digital image processor includes memory requirements.

11. The camera system of claim 10 wherein the memory requirements include:
   a memory space for a blemish factor;
   a memory space for a black pedestal factor;
   a memory space for a white shading factor; and
   a memory space for a white balance factor.

12. The camera system of claim 11 wherein the memory requirements further include:
   a memory space for a color matching factor;
   a memory space for an ELC factor;
   a memory space for a RGB spatial interpolation factor; and
   a memory space for a RGB to YCbCr factor.

13. The camera system of claim 12 wherein the memory requirements further include:
   a memory space for a horizontal aperture factor;
   a memory space for a motion adaptive deinteriacing factor;
   a memory space for a vertical aperture correction; and
   a memory space for a unsharp masking factor.

14. The camera system of claim 13 wherein the memory requirements further include:
   a memory space for a coring factor;
   a memory space for a level dependent noise suppression factor;
   a memory space for a digital zoom factor; and
   a memory space for a YCbCr to RGB factor.

15. The camera system of claim 14 wherein the memory requirements further include:
   a memory space for a RGB to HSV factor;
   a memory space for a hue control factor;
   a memory space for a saturation control factor; and
   a memory space for a HSV to RGB factor.

16. The camera system of claim 15 wherein the memory requirements further include:
   a memory space for a gamma/knee/decimation factor;
   a memory space for an hour meter factor; and
   a memory space for a camera serial number.

17. The camera system of claim 1 wherein calibration of the remote camera head occurs automatically upon coupling to the digital image processor.

* * * * *

UNITED STATES PATENT AND TRADEMARK OFFICE
CERTIFICATE OF CORRECTION

PATENT NO. : 9,866,742 B2  
APPLICATION NO. : 14/732852  
DATED : January 9, 2018  
INVENTOR(S) : Lim Cheung, Garry Womack and Jonathan Yuen Page 1 of 1

It is certified that error appears in the above-identified patent and that said Letters Patent is hereby corrected as shown below:

On the Title Page

Items (12) and (72), please correct the spelling of the name of the first inventor as follows:
-- Lim Cheung --.

Signed and Sealed this
Twenty-first Day of August, 2018

Andrei Iancu
*Director of the United States Patent and Trademark Office*